US012606810B2

(12) United States Patent
Gao et al.

(10) Patent No.: US 12,606,810 B2
(45) Date of Patent: Apr. 21, 2026

(54) SUBTILASE VARIANTS AND COMPOSITIONS COMPRISING SAME

(71) Applicant: Novozymes A/S, Bagsvaerd (DK)

(72) Inventors: Nan Gao, Beijing (CN); Carl Mikael Bauer, Malmo (SE); Esben Peter Friis, Herlev (DK); Rolf Thomas Lenhard, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 1064 days.

(21) Appl. No.: 17/426,569

(22) PCT Filed: Jan. 22, 2020

(86) PCT No.: PCT/CN2020/073760

§ 371 (c)(1),
(2) Date: Jul. 28, 2021

(87) PCT Pub. No.: WO2020/156419

PCT Pub. Date: Aug. 6, 2020

(65) Prior Publication Data

US 2022/0112476 A1 Apr. 14, 2022

(30) Foreign Application Priority Data

Jan. 28, 2019 (WO) ................ PCT/CN2019/073398

(51) Int. Cl.
*C12N 9/54* (2006.01)
*C11D 3/386* (2006.01)

(52) U.S. Cl.
CPC ................ *C12N 9/54* (2013.01); *C11D 3/386* (2013.01); *C12Y 304/21062* (2013.01)

(58) Field of Classification Search
None
See application file for complete search history.

(56) References Cited

U.S. PATENT DOCUMENTS

| | | | | |
|---|---|---|---|---|
| 4,661,452 A * | 4/1987 | Markussen | ........ | C11D 3/38672 510/451 |
| 2004/0147008 A1 | 7/2004 | Draborg | | |
| 2007/0161531 A1* | 7/2007 | Draborg | ............ | C11D 3/38636 435/254.2 |
| 2018/0148670 A1 | 5/2018 | O'connell | | |

FOREIGN PATENT DOCUMENTS

| | | | | |
|---|---|---|---|---|
| CN | 106661566 A | 5/2017 | | |
| CN | 107075493 A | 8/2017 | | |
| JP | 2009500023 A | 1/2009 | | |
| WO | WO-2004041979 A2 * | 5/2004 | ............ | C11D 3/386 |
| WO | 2007006305 A1 | 1/2007 | | |
| WO | 2016001449 A1 | 1/2016 | | |
| WO | 2016087617 A1 | 6/2016 | | |
| WO | 2018/118950 A1 | 6/2018 | | |

OTHER PUBLICATIONS

Timothy et al., 2004, Household & Personal Products Industry 41, 20-23.
OSTEN, 1993, Studies in organic chemistry, 133-144.
Novozymes A/S, 2013, IP.com No. IPCOM000231510D.

* cited by examiner

*Primary Examiner* — Todd M Epstein
(74) *Attorney, Agent, or Firm* — Kelly K. Reynolds

(57) ABSTRACT

Provided are subtilase variants having improved stability, detergent compositions comprising the variants, use of the variants and detergent compositions in a cleaning process such as laundry or hard surface cleaning such as dishwashing, and methods of producing the variants.

20 Claims, 1 Drawing Sheet

Specification includes a Sequence Listing.

```
SEQ01       1 AQSVPWGISRVQAPAAHNRGLTGSGVKVAVLDTGI-STHPDLNIRGGASF  49
              ||||| | |   ||| |  | ||| ||||| | || | ||||   ||||
SEQ02       1 AQSVPYGVSQIKAPALHSQGYTGSNVKVAVIDSGIDSSHPDLKVAGGASM  50

SEQ01      50 VPGEP-STQDGNGHGTHVAGTIAALNNSIGVLGVAPSAELYAVKVLGASG  98
              || |    || | |||||||| |||||||||||||||| ||||||||| |
SEQ02      51 VPSETNPFQDNNSHGTHVAGTVAALNNSIGVLGVAPSASLYAVKVLGADG 100

SEQ01      99 SGSVSSIAQGLEWAGNNGMHVANLSLGSPSPSATLEQAVNSATSRGVLVV 148
              ||  | |  | |||  | | | | ||| || || |  ||  |   || ||
SEQ02     101 SGQYSWIINGIEWAIANNMDVINMSLGGPSGSAALKAAVDKAVASGVVVV 150

SEQ01     149 AASGNSGA-GSIS---YPARYANAMAVGATDQNNNRASFSQYGAGLDIVA 194
              || || |  || |   ||  |    |||| |  | |||||  |  ||  |
SEQ02     151 AAAGNEGTSGSSSTVGYPGKYPSVIAVGAVDSSNQRASFSSVGPELDVMA 200

SEQ01     195 PGVNVQSTYPGSTYASLNGTSMATPHVAGAAALVKQKNPSWSNVQIRNHL 244
              |||  ||| ||  |   |||||| |||||||||   | | | | | |  |
SEQ02     201 PGVSIQSTLPGNKYGAYNGTSMASPHVAGAAALILSKHPNWTNTQVRSSL 250

SEQ01     245 KNTATSLGSTNLYGSGLVNAEAATR    269
               || | ||    || || |  ||
SEQ02     251 ENTTTKLGDSFYYGKGLINVQAAAQ    275
```

SUBTILASE VARIANTS AND COMPOSITIONS COMPRISING SAME

CROSS-REFERENCE TO RELATED APPLICATIONS

This application is a 35 U.S.C. 371 national application of PCT/CN2020/073760, filed Jan. 22, 2020, and published on Aug. 6, 2020 as WO 2020/156419, which application claims priority or the benefit from Chinese Patent Application No. PCT/CN2019/073398, filed Jan. 28, 2019. The contents of these applications are fully incorporated herein by reference.

REFERENCE TO A SEQUENCE LISTING

This application contains a sequence listing in computer readable form, which is incorporated herein by reference.

FIELD OF THE INVENTION

The present invention relates to subtilase variants, compositions comprising the variants, polynucleotides encoding the variants, methods of producing the variants, and methods of using the variants and compositions.

BACKGROUND OF THE INVENTION

Subtilisins are serine proteases from the family S8, in particular from the subfamily S8A, as defined by the MEROPS database (Hypertext transfer protocol world wide web address ebi.ac.uk/merops/index.shtml). In subfamily S8A the key active site residues Asp, His and Ser are typically found in motifs that differ from those of the S8B subfamily.

In the detergent industry, enzymes have for many decades been implemented in washing formulations. Enzymes used in such formulations comprise proteases, lipases, amylases, cellulases, mannosidases as well as other enzymes or mixtures thereof. Commercially, the most important enzymes are proteases.

An increasing number of commercially used proteases for e.g. laundry and dishwashing detergents are protein engineered variants of naturally occurring wild type proteases, Further, other subtilase variants have been described in the art with alterations relative to a parent subtilase resulting in improvements such as better wash performance, thermal stability, storage stability or catalytic activity.

However, various factors make further improvement of proteases advantageous. For example, washing conditions such as temperature and pH tend to change over time, and are also different in different countries or regions of the world, and many stains are still difficult to completely remove under conventional washing conditions. Another challenge in detergent compositions is enzyme stability, since the chemical components of these compositions as well as conditions of pH, temperature and humidity often tend to inactivate enzymes. Further, in-wash conditions can also result in inactivation of the enzymes (due to e.g. pH, temperature or chelation instability), resulting in loss of wash performance during the wash cycle. Thus, despite the intensive research in protease development there remains a need for new and improved proteases that have improved stability, for example improved storage stability, e.g. in a detergent composition, and which at the same time have similar or improved wash performance compared to the parent subtilase.

The present invention addresses these challenges by providing novel subtilase variants having advantageous properties in terms of stability and wash performance.

SUMMARY OF THE INVENTION

The present invention relates to novel subtilase variants suitable for use in e.g. detergent compositions, wherein the variants comprise substitutions in at least positions 9, 19 and 62 relative to SEQ ID NO: 1, in particular the substitutions S9R+R19L+N62D, for example the substitutions S3T+S9R+R19L+N62D+A194P.

The present invention also relates to compositions comprising the variants, in particular detergent compositions, polynucleotides encoding the variants; nucleic acid constructs, vectors, and host cells comprising the polynucleotides; and methods of producing the variants.

Overview of Sequences

SEQ ID NO: 1 is the amino acid sequence of the protease subtilisin 309, also known as Savinase®.

SEQ ID NO: 2 is the amino acid sequence of subtilisin BPN'.

BRIEF DESCRIPTION OF THE FIGURES

FIG. 1 is an alignment of the amino acid sequences of subtilisin 309 (SEQ ID NO: 1) and subtilisin BPN' (SEQ ID NO: 2).

DEFINITIONS

Subtilase/protease: The terms “subtilase” and “protease” may be used interchangeably herein and refer to an enzyme that hydrolyses peptide bonds in proteins. This includes any enzyme belonging to the EC 3.4 enzyme group (including each of the thirteen subclasses thereof), and in particular endopeptidases (EC 3.4.21). The EC number refers to Enzyme Nomenclature 1992 from NC-IUBMB, Academic Press, San Diego, California, including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively.

Protease activity: The term “protease activity” means a proteolytic activity (EC 3.4), in particular endopeptidase activity (EC 3.4.21). There are several protease activity types, the three main activity types being: trypsin-like, where there is cleavage of amide substrates following Arg or Lys at P1, chymotrypsin-like, where cleavage occurs following one of the hydrophobic amino acids at P1, and elastase-like with cleavage following an Ala at P1. Protease activity may be determined according to the procedure described in WO 2016/087619. The subtilisin variants of the present invention preferably have at least 80%, at least 90%, at least 95% or at least 100% of the protease activity of the polypeptide of SEQ ID NO: 1.

Allelic variant: The term “allelic variant” means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial primary RNA transcript is a precursor to mRNA that is processed through a series of steps, including splicing, before appearing as mature spliced mRNA.

Coding sequence: The term "coding sequence" means a polynucleotide which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more amino acids absent from the amino and/or carboxyl terminus of a mature polypeptide; wherein the fragment has subtilase activity. Such a fragment preferably contains at least 85%, at least 90% or at least 95% of the number of amino acids in SEQ ID NO: 1.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent protease, the protease with SEQ ID NO: 1, or a selected reference protease such as a variant of SEQ ID NO: 1. Such improved properties may include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity and thermostability. In one aspect the present invention, the improved property is improved stability, for example improved thermostability or improved storage stability in a detergent formulation or a defined pH stress buffer. In another aspect of the invention, the improved property is improved wash performance.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its mature form following N-terminal processing (e.g., removal of signal peptide).

Mature polypeptide coding sequence: The term "mature polypeptide coding sequence" means a polynucleotide that encodes a mature polypeptide having subtilase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent subtilase/protease: The term "parent" or "parent subtilase" or "parent protease" means any polypeptide with subtilase activity to which an alteration is made to produce the enzyme variants of the present invention. The parent may be a naturally occurring (wild-type) polypeptide or a variant thereof of a wild-type polypeptide. In a particular embodiment, the parent is a protease with at least 75% identity, such as at least 80%, at least 85%, at least 90%, at least 91%, at least 92%, at least 93%, at least 94%, at least 95%, at least 96%, at least 97%, at least 98% or at least 99% identity with SEQ ID NO: 1. Alternatively, the parent may have 100% identity to SEQ ID NO: 1.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having subtilase activity comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position.

Wild-type subtilase: The term "wild-type" subtilase means a subtilase expressed by a naturally occurring microorganism, such as a bacterium, yeast, or filamentous fungus found in nature.

Conventions for Designation of Variants

For purposes of the present invention, the polypeptide of SEQ ID NO: 2 is used to determine the corresponding amino acid residue in a subtilase variant of the invention. This is explained in more detail further below under the heading "Numbering of amino acid positions/residues".

Identification of the corresponding amino acid residue in another subtilase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

In describing the variants of the present invention, the nomenclature described below is adapted for ease of reference. The accepted IUPAC single letter or three letter amino acid abbreviation is employed. The terms "alteration" or "mutation" may be used interchangeably herein to refer to substitutions, insertions and deletions.

Substitutions. For an amino acid substitution, the following nomenclature is used: Original amino acid, position, substituted amino acid. For example, the substitution of a threonine at position 220 with alanine is designated as "Thr220Ala" or "T220A". Multiple substitutions may be separated by addition marks ("+"), e.g., "Thr220Ala+Gly229Val" or "T220A+G229V", representing substitutions at positions 220 and 229 of threonine (T) with alanine (A) and glycine (G) with valine (V), respectively. Multiple substitutions may alternatively be listed with individual mutations separated by a space or a comma. Alternative substitutions in a particular position may be indicated with a slash ("/"). For example, substitution of threonine in position 220 with either alanine, valine or leucine many be designated "T220A/V/L".

Substitutions may also be indicated with an "X" preceding a position number, which means that any original amino acid in a parent subtilase other than the subtilase of SEQ ID NO: 1 may be substituted at the corresponding indicated position in the parent subtilase. For example, "X19L" means that any amino acid residue at position 19 of a parent subtilase other than L is substituted with L.

Deletions. For an amino acid deletion, the following nomenclature is used: Original amino acid, position, *. Accordingly, the deletion of threonine at position 220 is designated as "Thr220*" or "T220*". Multiple deletions may be separated by addition marks ("+"), e.g., "Thr220*+Gly229*" or "T220*+G229*", or alternatively may be separated by a space or comma. The use of an "X" preceding a position number is as described above for substitutions, e.g. "X131*" means that the amino acid residue at position 131 is deleted.

Insertions. For an amino acid insertion, the following nomenclature is used: Original amino acid, position, original amino acid, inserted amino acid. Accordingly, the insertion of lysine after threonine at position 220 is designated "Thr220ThrLys" or "T220TK". An insertion of multiple amino acids is designated [Original amino acid, position, original amino acid, inserted amino acid #1, inserted amino acid #2; etc.]. For example, the insertion of lysine and alanine after threonine at position 220 is indicated as "Thr220ThrLysAla" or "T220TKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 220<br>T | 220 220a 220b<br>T - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Multiple alterations may alternatively be listed with individual mutations separated by a space or a comma.

Different alterations. Where different alterations can be introduced at a position, the different alterations may be separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Different alterations in a position may also be indicated with a slash ("/"), for example "T220A/V/L" as explained above. Alternatively, different alterations may be indicated using brackets, e.g., Arg170[Tyr, Gly] or in one-letter code R170 [Y,G].

Numbering of amino acid positions/residues. Amino acid position numbers as used herein are based on the numbering of the BPN' polypeptide of SEQ ID NO: 2. Thus, amino acid positions of a parent protease polypeptide having e.g. SEQ ID NO: 1 are those of the corresponding positions of SEQ ID NO: 2. This numbering system is conventional in the art, where position numbers used for subtilisin proteases in the patent literature are often based on the corresponding position numbers of BPN'.

Specifically, the numbering is based on the alignment in Table 1 of WO 89/06279, which shows an alignment of five proteases, including the mature polypeptide of the subtilase BPN' (BASBPN) sequence (sequence c in the table) and the mature polypeptide of subtilisin 309 from *Bacillus lentus*, also known as Savinase® (BLSAVI) (sequence a in the table).

The accompanying FIG. 1 is provided for reference purposes and shows an alignment between SEQ ID NO: 1 and SEQ ID NO: 2, based on Table 1 of WO 89/06279, from which position numbers corresponding to positions of SEQ ID NO: 2 may be readily determined.

For a parent protease other than SEQ ID NO: 1, the amino acid sequence of another protease may be similarly aligned with SEQ ID NO: 2 to determine amino acid position numbers corresponding to the numbering of SEQ ID NO: 2.

DETAILED DESCRIPTION OF THE INVENTION

Variants

In one aspect, the present invention relates to subtilase variant comprising the substitutions X9R+X19L+X62D, wherein (a) position numbers correspond to positions of the polypeptide of SEQ ID NO: 2;
(b) the variant has protease activity; and
(c) the variant has at least 80%, e.g. at least 85% at least 90%, at least 91%, at least 92%, at least 93%, at least 94%, at least 95%, at least 96%, at least 97% or at least 98% but less than 100% sequence identity to the polypeptide of SEQ ID NO: 1;

and with the proviso that the variant does not comprise a histidine residue in position 14.

In a particular aspect, the present invention relates to subtilase variant comprising the substitutions X3T+X9R+X19L+X62D+X194P, wherein (a) position numbers correspond to positions of the polypeptide of SEQ ID NO: 2;
(b) the variant has protease activity; and
(c) the variant has at least 80% but less than 100% sequence identity to the polypeptide of SEQ ID NO: 1.

In one embodiment of this aspect, the substitutions X3T+X9R+X19L+X62D+X194P are S3T+S9R+R19L+N62D+A194P.

Thus, in one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+A194P.

In a preferred embodiment, the subtilase variant comprises or consists of the polypeptide of SEQ ID NO: 1 with the substitutions S3T+S9R+R19L+N62D+A194P.

In some embodiments, the subtilase variant further comprises at least one alteration selected from the group consisting of N43R, N76D, P131*, Q245R, S259D and R275Q, wherein position numbers correspond to positions of the polypeptide of SEQ ID NO: 2. Non-limiting examples of such variants are provided below.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+A194P+Q245R+S259D.

In a preferred embodiment, the subtilase variant comprises or consists of the polypeptide of SEQ ID NO: 1 with the substitutions S3T+S9R+R19L+N62D+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+A194P+R275Q.

In a particular embodiment, the subtilase variant comprises or consists of the polypeptide of SEQ ID NO: 1 with the substitutions S3T+S9R+R19L+N43R+N62D+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+P131*+A194P.

In a particular embodiment, the subtilase variant comprises or consists of the polypeptide of SEQ ID NO: 1 with the substitutions S3T+S9R+R19L+N62D+P131*+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+P131*+A194P+Q245R+S259D.

In a particular embodiment, the subtilase variant comprises or consists of the polypeptide of SEQ ID NO: 1 with the substitutions S3T+S9R+R19L+N62D+P131*+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+P131*+A194P+R275Q.

In a particular embodiment, the subtilase variant comprises or consists of the polypeptide of SEQ ID NO: 1 with the substitutions S3T+S9R+R19L+N43R+N62D+P131*+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+N76D+A194P.

In a particular embodiment, the subtilase variant comprises or consists of the polypeptide of SEQ ID NO: 1 with the substitutions S3T+S9R+R19L+N43R+N62D+N76D+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+N76D+P131*+A194P.

In a particular embodiment, the subtilase variant comprises or consists of the polypeptide of SEQ ID NO: 1 with the substitutions S3T+S9R+R19L+N43R+N62D+N76D+P131*+A194P.

As indicated above, in one aspect of the invention the subtilase variants do not comprise a histidine residue in position 14.

In an embodiment of the broad aspect of the invention described above relating to a subtilase variant comprising the substitutions X9R+X19L+X62D, and where the variant does not comprise a histidine residue in position 14, the substitutions X9R+X19L+X62D are S9R+R19L+N62D.

In some embodiments of this aspect, the subtilase variant further comprises at least one alteration selected from the group consisting of S3T, 53A, N43R, V68A, N76D, P131*, A194P, V205I, Q245R, S259D, N261D and R275Q, preferably two, three or more of said alterations, such as four, five, six or more of said alterations, wherein position numbers correspond to positions of the polypeptide of SEQ ID NO: 2. Non-limiting examples of such variants are provided below.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+Q245R+S259D.

In a particular embodiment, the subtilase variant comprises or consists of the polypeptide of SEQ ID NO: 1 with the substitutions S3T+S9R+R19L+N62D+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+R275Q.

In a particular embodiment, the subtilase variant comprises or consists of the polypeptide of SEQ ID NO: 1 with the substitutions S3T+S9R+R19L+N43R+N62D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+P131*.

In a particular embodiment, the subtilase variant comprises or consists of the polypeptide of SEQ ID NO: 1 with the substitutions S3T+S9R+R19L+N62D+P131*.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N62D+P131*+Q245R+S259D.

In a particular embodiment, the subtilase variant comprises or consists of the polypeptide of SEQ ID NO: 1 with the substitutions S3T+S9R+R19L+N62D+P131*+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+P131*+R275Q.

In a particular embodiment, the subtilase variant comprises or consists of the polypeptide of SEQ ID NO: 1 with the substitutions S3T+S9R+R19L+N43R+N62D+P131*+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+N76D.

In a particular embodiment, the subtilase variant comprises or consists of the polypeptide of SEQ ID NO: 1 with the substitutions S3T+S9R+R19L+N43R+N62D+N76D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+N76D+Q245R+S259D.

In a particular embodiment, the subtilase variant comprises or consists of the polypeptide of SEQ ID NO: 1 with the substitutions S3T+S9R+R19L+N43R+N62D+N76D+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3T+S9R+R19L+N43R+N62D+N76D+P131*.

In a particular embodiment, the subtilase variant comprises or consists of the polypeptide of SEQ ID NO: 1 with the substitutions S3T+S9R+R19L+N43R+N62D+N76D+P131*.

In one embodiment, the subtilase variant has at least 80%, e.g. at least 85%, at least 90%, at least 91%, at least 92%, at least 93%, at least 94%, at least 95% or at least 96% but less than 100% sequence identity to the polypeptide of SEQ ID NO: 1 and comprises the substitutions S9R+A15T+G61E+N62D+V68A+A194P+V205I+Q245R+N261D. In a particular embodiment, the subtilase variant comprises or consists of the polypeptide of SEQ ID NO: 1 with the substitutions S9R+A15T+G61E+N62D+V68A+A194P+V205I+Q245R+N261D.

In one embodiment, the subtilase variant has at least 80%, e.g. at least 85%, at least 90%, at least 91%, at least 92%, at least 93%, at least 94%, at least 95% or at least 96% but less than 100% sequence identity to the polypeptide of SEQ ID NO: 1 and comprises the substitutions S9R+A15T+G61E+V68A+A194P+V205I+Q245R+S259D+N261D.

In a particular embodiment, the subtilase variant comprises or consists of the polypeptide of SEQ ID NO: 1 with the substitutions S9R+A15T+G61E+V68A+A194P+V205I+Q245R+S259D+N261D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+R275Q.

In a particular embodiment, the subtilase variant comprises or consists of the polypeptide of SEQ ID NO: 1 with the substitutions S9R+R19L+N43R+N62D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N62D+P131*.

In a particular embodiment, the subtilase variant comprises or consists of the polypeptide of SEQ ID NO: 1 with the substitutions S9R+R19L+N62D+P131*.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+Q245R+S259D.

In a particular embodiment, the subtilase variant comprises or consists of the polypeptide of SEQ ID NO: 1 with the substitutions S3A+S9R+R19L+N62D+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+A194P.

In a particular embodiment, the subtilase variant comprises or consists of the polypeptide of SEQ ID NO: 1 with the substitutions S3A+S9R+R19L+N62D+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+Q245R+S259D+R275Q.

In a particular embodiment, the subtilase variant comprises or consists of the polypeptide of SEQ ID NO: 1 with the substitutions S9R+R19L+N43R+N62D+Q245R+S259D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N62D+P131*+Q245R+S259D.

In a particular embodiment, the subtilase variant comprises or consists of the polypeptide of SEQ ID NO: 1 with the substitutions S9R+R19L+N62D+P131*+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+A194P+R275Q.

In a particular embodiment, the subtilase variant comprises or consists of the polypeptide of SEQ ID NO: 1 with the substitutions S9R+R19L+N43R+N62D+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N62D+P131*+A194P.

In a particular embodiment, the subtilase variant comprises or consists of the polypeptide of SEQ ID NO: 1 with the substitutions S9R+R19L+N62D+P131*+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D.

In a particular embodiment, the subtilase variant comprises or consists of the polypeptide of SEQ ID NO: 1 with the substitutions S9R+R19L+N43R+N62D+N76D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+Q245R+S259D+R275Q.

In a particular embodiment, the subtilase variant comprises or consists of the polypeptide of SEQ ID NO: 1 with the substitutions S3A+S9R+R19L+N43R+N62D+Q245R+S259D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+P131*+Q245R+S259D.

In a particular embodiment, the subtilase variant comprises or consists of the polypeptide of SEQ ID NO: 1 with the substitutions S3A+S9R+R19L+N62D+P131*+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+A194P+Q245R+S259D.

In a particular embodiment, the subtilase variant comprises or consists of the polypeptide of SEQ ID NO: 1 with the substitutions S3A+S9R+R19L+N62D+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+P131*+R275Q.

In a particular embodiment, the subtilase variant comprises or consists of the polypeptide of SEQ ID NO: 1 with the substitutions S3A+S9R+R19L+N43R+N62D+P131*+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+A194P+R275Q.

In a particular embodiment, the subtilase variant comprises or consists of the polypeptide of SEQ ID NO: 1 with the substitutions S3A+S9R+R19L+N43R+N62D+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+P131*+A194P In a particular embodiment, the subtilase variant comprises or consists of the polypeptide of SEQ ID NO: 1 with the substitutions S3A+S9R+R19L+N62D+P131*+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+N76D In a particular embodiment, the subtilase variant comprises or consists of the polypeptide of SEQ ID NO: 1 with the substitutions S3A+S9R+R19L+N43R+N62D+N76D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+P131*+Q245R+S259D+R275Q.

In a particular embodiment, the subtilase variant comprises or consists of the polypeptide of SEQ ID NO: 1 with the substitutions S9R+R19L+N43R+N62D+P131*+Q245R+S259D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+A194P+Q245R+S259D+R275Q.

In a particular embodiment, the subtilase variant comprises or consists of the polypeptide of SEQ ID NO: 1 with the substitutions S9R+R19L+N43R+N62D+A194P+Q245R+S259D+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N62D+P131*+A194P+Q245R+S259D.

In a particular embodiment, the subtilase variant comprises or consists of the polypeptide of SEQ ID NO: 1 with the substitutions S9R+R19L+N62D+P131*+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+Q245R+S259D.

In a particular embodiment, the subtilase variant comprises or consists of the polypeptide of SEQ ID NO: 1 with the substitutions S9R+R19L+N43R+N62D+N76D+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+P131*+A194P+R275Q.

In a particular embodiment, the subtilase variant comprises or consists of the polypeptide of SEQ ID NO: 1 with the substitutions S9R+R19L+N43R+N62D+P131*+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+P131*.

In a particular embodiment, the subtilase variant comprises or consists of the polypeptide of SEQ ID NO: 1 with the substitutions S9R+R19L+N43R+N62D+N76D+P131*.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+A194P.

In a particular embodiment, the subtilase variant comprises or consists of the polypeptide of SEQ ID NO: 1 with the substitutions S9R+R19L+N43R+N62D+N76D+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N62D+P131*+A194P+Q245R+S259D.

In a particular embodiment, the subtilase variant comprises or consists of the polypeptide of SEQ ID NO: 1 with the substitutions S3A+S9R+R19L+N62D+P131*+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+N76D+Q245R+S259D.

In a particular embodiment, the subtilase variant comprises or consists of the polypeptide of SEQ ID NO: 1 with the substitutions S3A+S9R+R19L+N43R+N62D+N76D+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+P131*+A194P+R275Q.

In a particular embodiment, the subtilase variant comprises or consists of the polypeptide of SEQ ID NO: 1 with the substitutions S3A+S9R+R19L+N43R+N62D+P131*+A194P+R275Q.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+N76D+P131*.

In a particular embodiment, the subtilase variant comprises or consists of the polypeptide of SEQ ID NO: 1 with the substitutions S3A+S9R+R19L+N43R+N62D+N76D+P131*.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S3A+S9R+R19L+N43R+N62D+N76D+A194P.

In a particular embodiment, the subtilase variant comprises or consists of the polypeptide of SEQ ID NO: 1 with the substitutions S3A+S9R+R19L+N43R+N62D+N76D+A194P.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+P131*+Q245R+S259D.

In a particular embodiment, the subtilase variant comprises or consists of the polypeptide of SEQ ID NO: 1 with the substitutions S9R+R19L+N43R+N62D+N76D+P131*+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+A194P+Q245R+S259D.

In a particular embodiment, the subtilase variant comprises or consists of the polypeptide of SEQ ID NO: 1 with the substitutions S9R+R19L+N43R+N62D+N76D+A194P+Q245R+S259D.

In one embodiment, the subtilase variant has at least 80%, e.g. at least 85%, at least 90%, at least 91%, at least 92%, at least 93%, at least 94%, at least 95%, at least 96% or at least 97% but less than 100% sequence identity to the polypeptide of SEQ ID NO: 1 and comprises the substitutions S9R+R19L+N43R+N62D+N76D+P131*+A194P.

In a particular embodiment, the subtilase variant comprises or consists of the polypeptide of SEQ ID NO: 1 with the substitutions S9R+R19L+N43R+N62D+N76D+P131*+A194P.

In one aspect, the subtilase variant may comprise 2-6, such as 3, 4 or 5, histidine residues added to the N-terminal or the C-terminal. An example of such a variant is one that comprises SEQ ID NO: 1 with the substitutions S3T+S9R+R19L+N62D+A194P+R275RHHHH, where "R275RHHHH" indicates four additional histidine residues after the C-terminal Arg residue.

In addition to the amino acid alterations specifically disclosed herein, a protease variant of the invention may comprise additional alterations at one or more other positions. These additional alterations may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, in *The Proteins*, Academic Press, New York. Common conservative substitution groups include, but are not limited to: G=A=S; I=V=L=M; D=E; Y=F; and N=Q (where e.g. "G=A=S" means that these three amino acids may be substituted for each other).

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one aspect of the invention, the protease variant has at least one improved property compared to a reference protease, where the reference protease may e.g. be the protease of SEQ ID NO: 1 or a variant thereof.

In one embodiment, the protease variant of the invention has an improved stability, for example improved thermostability, improved storage stability in a detergent formulation or improved stability in a defined pH stress buffer.

Improved stability may e.g. be determined as described in the examples herein using one or both of the following assays:

stability assay using a low pH (pH 4.0) stress buffer stability assay using a high pH (pH 10.5) stress buffer and LAS.

Stability may also be measured as stability in a detergent composition, for example in a powder detergent composition, e.g. a powder model laundry detergent composition containing the ingredients set forth in Table 3 herein. For example, a protease variant may be tested in the powder model laundry detergent composition of Table 3 in an accelerated storage stability assay, where the detergent composition is stored for e.g. 2 weeks or 4 weeks at 37° C. and a relative humidity of 70%. In this case, the protease may be added to the powder detergent composition in the form of a granulate, e.g. comprising a coating such as an inorganic salt coating; for more information, see below under the heading "Granular detergent formulations". The proteolytic activity is determined before and after storage, and the residual activity after storage is calculated based on the initial activity. Proteolytic activity may be determined using the Suc-AAPF-pNA activity assay; see below in the examples section for a description of this assay.

An improved stability may e.g. be expressed as a half-life improvement factor (T½ IF), which is calculated as the half-life of a protease variant relative to the half-life of a reference protease.

In one embodiment, the stability of a protease variant of the invention is determined as a half-life improvement factor (T½ IF) relative to the half-life of a variant of SEQ ID NO: 1 having the substitutions S9R, P14H, R19L and N62D. In this embodiment, the protease variant of the invention preferably has a half-life improvement factor of at least about 1.2, more preferably at least about 1.5, such as at least about 2.0, at least about 3, at least about 4, at least about 5, at least about 6, at least about 7, at least about 8, at least about 9 or at least about 10, in at least one stability assay.

In one embodiment, the protease variant of the invention has a half-life improvement factor (T½ IF), relative to the half-life of a variant of SEQ ID NO: 1 having the substitutions S9R, P14H, R19L and N62D, of at least about 2, such as at least about 3, at least about 4, at least about 5, at least about 6, at least about 7, at least about 8, at least about 9 or at least about 10, in the low pH stability assay described in Example 2 herein.

In one embodiment, the protease variant of the invention has a half-life improvement factor (T½ IF), relative to the half-life of a variant of SEQ ID NO: 1 having the substitutions S9R, P14H, R19L and N62D, of at least about 1.2, preferably at least about 1.3, more preferably at least about 1.4, such as at least about 1.5, at least about 2, at least about 3 or at least about 4, in the high pH+LAS stability assay described in Example 2 herein.

In a preferred embodiment, the protease variant of the invention has an improved stability in both the low pH stability assay and the high pH+LAS stability assay described in Example 2 herein. For example, the protease variant may have a half-life improvement factor (T½ IF), relative to the half-life of a variant of SEQ ID NO: 1 having the substitutions S9R, P14H, R19L and N62D, of at least about 2, such as at least about 3, at least about 4, at least about 5, at least about 6, at least about 7, at least about 8, at least about 9 or at least about 10, in the low pH stability assay described in Example 2 herein; and a half-life improvement factor (T½ IF), relative to the half-life of a variant of SEQ ID NO: 1 having the substitutions S9R, P14H, R19L and N62D, of at least about 1.2, preferably at least about 1.3, more preferably at least about 1.4, such as at least about 1.5, at least about 2, at least about 3 or at least about 4, in the high pH+LAS stability assay described in Example 2 herein.

In another embodiment, the protease variant of the invention preferably has a half-life improvement factor, relative to the half-life of a variant of SEQ ID NO: 1 having the substitutions S9R, P14H, R19L and N62D, of at least about 1.2, more preferably at least about 1.5, such as at least about 2, at least about 3, at least about 4 or at least about 5, in an accelerated storage stability assay in a powder detergent composition. The accelerated storage stability assay may for example comprise storage for e.g. 2 weeks or 4 weeks at 37° C. and a relative humidity of 70%, where the enzyme is added to the powder detergent composition in the form of a granulate, e.g. comprising a coating such as an inorganic salt coating; for more information, see below under the heading "Granular detergent formulations".

In another aspect of the invention, the protease variant has a wash performance that is improved compared to that of a reference protease, where the reference protease may e.g. be the protease of SEQ ID NO: 1. An improved wash performance in this context may be defined as an improved relative wash performance on the EMPA117EH stain, for example determined with the AMSA assay as described in Example 3 herein using a protease concentration of 10 nM or 20 nM and compared to a reference protease with SEQ ID NO: 1, of at least about 1.1, preferably at least about 1.2, more preferably at least about 1.3, such as at least about 1.4, at least about 1.5 or at least about 1.6.

In one embodiment, the protease variant has an improved relative wash performance on the PC-03 stain, for example determined with the AMSA assay as described in Example 3 herein using a protease concentration of 10 nM or 20 nM and compared to a reference protease with SEQ ID NO: 1, of at least about 1.0, such as least about 1.1, preferably at least about 1.2, more preferably at least about 1.3, such as at least about 1.4.

In another embodiment, improved wash performance may be defined as a relative wash performance in any of the stains PC-03, PC-05, EMPA116 and/or EMPA117EH, determined with the TOM assay as described in Example 4 herein compared to a reference protease with SEQ ID NO: 1, of at least about 1.2, preferably at least about 1.3, more preferably at least about 1.4, such as at least about 1.5, at least about 1.6, at least about 1.7, at least about 1.8, at least about 1.9 or at least about 2.0. The improved wash performance in TOM relative to SEQ ID NO: 1 may, for example, be a relative wash performance of at least about 1.5, at least about 1.8, at least about 2.0 or at least about 2.2 in the EMPA117EH stain, and/or in the PC-03 stain.

Parent Subtilases

The parent subtilase of a variant of the invention will typically be a protease that has at least 75% identity with the subtilase of SEQ ID NO: 1. In preferred embodiments, the parent subtilase may have at least 80% identity to SEQ ID NO: 1, such as at least 85%, at least 90%, at least 91%, at least 92%, at least 93%, at least 94%, at least 95%, at least 96%, at least 97%, at least 98% or at least 99% identity with SEQ ID NO: 1. Alternatively, the parent subtilase may have a sequence that comprises of consists of SEQ ID NO: 1.

The parent may thus, for example, have the sequence of the subtilase of SEQ ID NO: 1, or alternatively may be a variant of SEQ ID NO: 1. The parent may also be a related subtilase, e.g. from the S8A family having at least 75% sequence identity to SEQ ID NO: 1 as indicated above.

In one embodiment, the amino acid sequence of the parent may for example differ by up to 20 amino acids, such as up to 10 amino acids, e.g., 1, 2, 3, 4, 5, 6, 7, 8, 9 or 10 amino acids, from the polypeptide of SEQ ID NO: 1.

The parent subtilase may also be a fragment of the polypeptide of SEQ ID NO: 1 that has protease activity, or an allelic variant of the polypeptide of SEQ ID NO: 1.

The parent subtilase may be obtained from a microorganism of any suitable genus, in particular from a suitable bacteria genus. The parent subtilase is thus typically a bacterial subtilase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus* or *Streptomyces* subtilase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* subtilase.

In one embodiment, the parent is obtained from a species of *Bacillus*. The parent may thus e.g. be a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis* or *Bacillus thuringiensis* subtilase.

In one embodiment, the parent is a protease derived from *Bacillus lentus* or a variant thereof, e.g. the protease of SEQ ID NO: 1.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, compost, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., *Molecular Cloning;* 3rd Ed., 2001, Cold Spring Harbor Laboratory Press).

Preparation of Variants

The present invention also relates to methods for obtaining a subtilase variant as described herein.

One embodiment relates to a method for obtaining a subtilase variant, the method comprising:

(a) providing a host cell comprising a polynucleotide encoding a variant of a parent protease comprising the mutations X9R+X19L+X62D compared to SEQ ID NO: 1, wherein position numbers correspond to positions of the polypeptide of SEQ ID NO: 2, wherein the variant has protease activity and a sequence identity to SEQ ID NO: 1 of at least 80% but less than 100%, and with the proviso that the variant does not comprise a histidine residue in position 14;

(b) cultivating the host cell under conditions suitable for expression of the variant; and (c) recovering the variant.

In a particular embodiment, the method for obtaining a subtilase variant comprises:

(a) providing a host cell comprising a polynucleotide encoding a variant of a parent protease comprising the mutations X3T+X9R+X19L+X62D+X194P compared to SEQ ID NO: 1, wherein position numbers correspond to positions of the polypeptide of SEQ ID NO: 2, and wherein the variant has protease activity and a sequence identity to SEQ ID NO: 1 of at least 80% but less than 100%;

(b) cultivating the host cell under conditions suitable for expression of the variant; and (c) recovering the variant.

The variants can be prepared using any mutagenesis procedure known in the art, such as site-directed mutagenesis, synthetic gene construction, semi-synthetic gene construction, random mutagenesis, DNA shuffling, etc. For information on use of these mutagenesis techniques, see e.g. WO 2017/207762.

It will be understood that the method for obtaining a subtilase variant is meant to encompass expression and recovery of variants having any combination of mutations disclosed above under the heading "Variants".

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for and optimize expression of a variant. Techniques for modifying polynucleotides utilizing recombinant DNA methods are well known in the art. These include, e.g., the use of control sequences such as promoters, transcription terminators, mRNA stabilizer regions downstream of a promoter and upstream of the coding sequence, signal peptide coding regions, propeptide coding sequences and regulatory sequences. For further information, see e.g. WO 2017/207762.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

For information on expression vectors, see e.g. WO 2017/207762.

Host Cells

The present invention also relates to recombinant host cells comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell will typically be a Gram-positive or Gram-negative bacterium, such as a Gram-positive bacterium selected from *Bacillus, Clostridium, Enterococcus, Geobacillus, Lactobacillus, Lactococcus, Oceanobacillus, Staphylococcus, Streptococcus* and *Streptomyces*, or a Gram-negative bacterium selected from *Campylobacter, E. coli, Flavobacterium, Fusobacterium, Helicobacter, Ilyobacter, Neisseria, Pseudomonas, Salmonella* and *Ureaplasma.*

The bacterial host cell may e.g. be a *Bacillus* cell selected from *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis* and *Bacillus thuringiensis* cells.

For information on suitable host cells, see e.g. WO 2017/207762.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid-state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity, and may be recovered and purified using methods known in the art. See e.g. WO 2017/207762 for further information.

Compositions

The invention also relates to a composition comprising a subtilase variant of the invention, e.g. a detergent or cleaning composition.

The invention also relates to a composition comprising a subtilase variant of the invention and further comprising: one or more detergent components; and/or one or more additional enzymes. In a preferred embodiment, the composition is a detergent composition comprising one or more detergent components, in particular one or more non-naturally occurring detergent components.

The present invention also relates to a composition comprising a subtilase variant of the present invention and further comprising one or more additional enzymes selected from the group consisting of amylases, catalases, cellulases (e.g., endoglucanases), cutinases, haloperoxygenases, lipases, mannanases, pectinases, pectin lyases, peroxidases, proteases, xanthanases, lichenases and xyloglucanases, or any mixture thereof.

A detergent composition may e.g. be in the form of a bar, a homogeneous tablet, a tablet having two or more layers, a pouch having one or more compartments, a regular or compact powder, a granule, a paste, a gel, or a regular, compact or concentrated liquid.

In one preferred embodiment, the detergent composition is a powder composition.

The invention also relates to use of a composition of the present in a cleaning process, such as laundry or hard surface cleaning such as dishwashing.

The choice of additional components for a detergent composition is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product.

In a particular embodiment, a detergent composition comprises a subtilase variant of the invention and one or more non-naturally occurring detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

In one embodiment, the subtilase variant of the invention may be added to a detergent composition in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

An automatic dish wash (ADVV) composition may for example include 0.001%-30%, such as 0.01%-20%, such as 0.1-15%, such as 0.5-10% of enzyme protein by weight of the composition.

A granulated composition for laundry may for example include 0.001%-20%, such as 0.01%-10%, such as 0.05%-5% of enzyme protein by weight of the composition.

A liquid composition for laundry may for example include 0.0001%-10%, such as 0.001-7%, such as 0.1%-5% of enzyme protein by weight of the composition.

The enzymes such as the subtilase variant of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708 or the variants according to the invention may be stabilized using peptide aldehydes or ketones such as described in WO 2005/105826 and WO 2009/118375.

The subtilase variants of the invention may be formulated in liquid laundry compositions such as a liquid laundry compositions composition comprising:

a) at least 0.01 mg of active subtilase variant per liter detergent, b) 2 wt % to 60 wt % of at least one surfactant c) 5 wt % to 50 wt % of at least one builder The detergent composition may be formulated into a granular detergent for laundry. Such detergent may comprise;

a) at least 0.01 mg of active protease variant per gram of composition b) anionic surfactant, preferably 5 wt % to 50 wt % c) nonionic surfactant, preferably 1 wt % to 8 wt % d) builder, preferably 5 wt % to 40 wt %, such as carbonates, zeolites, phosphate builder, calcium sequestering builders or complexing agents.

Although components mentioned below are categorized by general header according to a particular functionality, this is not to be construed as a limitation, as a component may comprise additional functionalities as will be appreciated by the person skilled in the art.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized. Surfactants lower the surface tension in the detergent, which allows the stain being cleaned to be lifted and dispersed and then washed away.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein, the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein, the detergent will usually contain from about 0% to about 10% by weight of a zwitterionic surfactant. Non-limiting examples of zwitterionic surfactants include betaine, alkyldimethylbetaine, sulfobetaine, and combinations thereof.

Builders and Co-Builders

The detergent composition may contain about 0-65% by weight, such as about 5% to about 45% of a detergent builder or co-builder, or a mixture thereof. In a dish wash detergent, the level of builder is typically 40-65%, particularly 50-65%. Builders and chelators soften, e.g., the wash water by removing the metal ions form the liquid. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl) iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N', N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854 and U.S. Pat. No. 5,977,053.

The subtilase variants of the invention may also be formulated into a dish wash composition, preferably an automatic dish wash composition (ADVV), comprising:

a) at least 0.01 mg of active protease variant according to the invention, and
b) 10-50 wt % builder preferably selected from citric acid, methylglycine-N,N-diacetic acid (MGDA) and/or glutamic acid-N,N-diacetic acid (GLDA) and mixtures thereof, and
c) at least one bleach component.

Bleaching Systems

The detergent may contain 0-50% by weight, such as about 0.1% to about 25%, of a bleaching system. Bleach systems remove discolor often by oxidation, and many bleaches also have strong bactericidal properties, and are used for disinfecting and sterilizing. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator.

The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy] benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that it is environmentally friendly as it eventually degrades into citric acid and alcohol. Furthermore, acetyl triethyl citrate and triacetin have good hydrolytic stability in the product upon storage and are efficient bleach activators. Finally, ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst or a booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn (O)3Mn(Me3-TACN)](PF6)2, and [2,2',2"-nitrilotris(ethane-1,2-diylazanylylidene-KN-methanylylidene)triphenolato-κ3O]manganese(III). The bleach catalysts may also be other metal compounds, such as iron or cobalt complexes.

In some embodiments, the bleach component may be an organic catalyst selected from the group consisting of organic catalysts having the following formula:

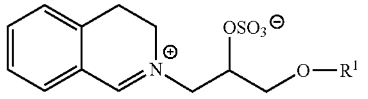

(i)

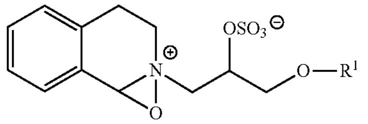

(ii)

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Hydrotropes

A hydrotrope is a compound that solubilizes hydrophobic compounds in aqueous solutions (or oppositely, polar substances in a non-polar environment). Typically, hydrotropes have both hydrophilic and hydrophobic characters (so-called amphiphilic properties as known from surfactants); however, the molecular structures of hydrotropes generally do not favour spontaneous self-aggregation, see, e.g., review by Hodgdon and Kaler, 2007, Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behaviour, stability, and colloidal properties of systems containing substances of polar and non-polar character, including mixtures of water, oil, surfactants, and polymers. Hydrotropes are classically used across industries from pharma, personal care and food to technical applications. Use of hydrotropes in detergent compositions allows for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when the fabric is contacted with a wash liquor comprising the detergent compositions and thus altering the tint of the fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt % to 0.2 wt. % fabric hueing agent, this may be especially preferred when the composition is in the form of a unit dose pouch. Suitable hueing agents are also disclosed in, e.g., WO 2007/087257 and WO 2007/087243.

Additional Enzymes

A detergent additive or detergent composition comprising the subtilase variant of the invention may comprise one or more enzymes such as an amylase, arabinase, carbohydrase, cellulase (e.g., endoglucanase), cutinase, galactanase, haloperoxygenase, lipase, mannanase, oxidase, e.g., laccase and/or peroxidase, pectinase, pectin lyase, protease, xylanase, xanthanase or xyloglucanase.

The properties of the selected enzyme(s) should be compatible with the selected detergent (e.g. pH-optimum, compatibility with other enzymatic and non-enzymatic ingredients, etc.).

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 495257, EP 531372, WO 96/11262, WO 96/29397, WO 98/08940. Other examples are cellulase variants such as those described in WO 94/07998, EP 531315, U.S. Pat. Nos. 5,457,046, 5,686,593, 5,763,254, WO 95/24471, WO 98/12307 and PCT/DK98/00299.

Examples of cellulases exhibiting endo-beta-1,4-glucanase activity (EC 3.2.1.4) are described in WO 02/99091.

Other examples of cellulases include the family 45 cellulases described in WO 96/29397, and especially variants thereof having substitution, insertion and/or deletion at one or more of the positions corresponding to the following positions in SEQ ID NO: 8 of WO 02/99091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases

The composition may comprise one or more additional proteases including those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteasemay for example be a thermolysin from, e.g., family M4 or other metalloprotease such as those from M5, M7 or M8 families.

Examples of metalloproteases are the neutral metalloproteases as described in WO 2007/044993 (Genencor Int.) such as those derived from *Bacillus amyloliquefaciens*.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase®, Esperase® and Progress® Excel (Novozymes A/S), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser®, Opticlean® and Optimase® (Danisco/DuPont), Axapem™ (Gist-Brocades N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), P. sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Amylases

Suitable amylases which can be used together with the subtilase variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylases comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+I201F+A209V+Q264S.

Other suitable amylases are amylases having the sequence of SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K, wherein the variants are C-terminally truncated and optionally further comprise a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, 1203, S241, R458, T459, D460, G476 and G477. More preferred variants of SEQ ID NO: 1 are those having the substitution in one of more of the following positions: K176L, E187P, N192FYH, M199L, 1203YF, S241QADN, R458N, T459S, D460T, G476K and G477K and/or a deletion in position R178 and/or S179 or of T180 and/or G181. Most preferred amylase variants of SEQ ID NO: 1 comprise the substitutions:

E187P+I203Y+G476K
E187P+I203Y+R458N+T459S+D460T+G476K and optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, 1181, G182, M200, L204, E242, G477 and G478.

More preferred variants of SEQ ID NO: 1 are those having the substitution in one of more of the following positions: N21D, D97N, V128I K177L, M200L, L204YF, E242QA, G477K and G478K and/or a deletion in position R179 and/or S180 or of I181 and/or G182. Most preferred amylase variants of SEQ ID NO: 1 comprise the substitutions N21D+D97N+V128I, and optionally further comprise a substitution at position 200 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particularly preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants: The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant Science Series, volume 71, Marcel Dekker, Inc., 1997.

Dye Transfer Inhibiting Agents: The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent: The detergent compositions of the present invention will preferably also contain additional components that may tint articles being cleaned, such as fluorescent whitening agent or optical brighteners. Where present the brightener is preferably at a level of about 0.01% to about 05%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino)

stilbene-2,2'-disulphonate and 2-(stilbyl-4"-naptho-1.,2':4, 5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl)disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil release polymers: The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 03/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents: The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent enzyme(s), i.e. a subtilase variant of the invention and optionally one or more additional enzymes, may be included in a detergent composition by adding separate additives containing one or more enzymes, or by adding a combined additive comprising all of these enzymes. A detergent additive comprising one or more enzymes can be formulated, for example, as a granulate, liquid, slurry, etc. Preferred detergent additive formulations include granulates, in particular non-dusting granulates, liquids, in particular stabilized liquids, or slurries.

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multiple compartments. It can be of any form, shape and material which is suitable for hold the composition, e.g., without allowing the release of the composition from the pouch prior to water contact. The pouch is made from water soluble film which encloses an inner volume. The inner volume can be divided into compartments of the pouch. Preferred films are polymeric materials, preferably polymers which are formed into a film or sheet. Preferred polymers, copolymers or derivates thereof are selected from polyacrylates, and water-soluble acrylate copolymers, methyl cellulose, carboxy methyl cellulose, sodium dextrin, ethyl cellulose, hydroxyethyl cellulose, hydroxypropyl methyl cellulose, maltodextrin, polymethacrylates, most preferably polyvinyl alcohol copolymers and hydroxypropyl methyl cellulose (HPMC). Preferably the level of polymer in the film for example PVA is at least about 60%. The preferred average molecular weight will typically be about 20,000 to about 150,000. Films can also be of blend compositions comprising hydrolytically degradable and water-soluble polymer blends such as polylactide and polyvinyl alcohol (known under the Trade reference M8630 as sold by Chris Craft In. Prod. of Gary, Ind., US) plus plasticizers like glycerol, ethylene glycerol, propylene glycol, sorbitol and mixtures thereof. The pouches can comprise a solid laundry detergent composition or part components and/or a liquid cleaning composition or part components separated by the water-soluble film. The compartment for liquid components can be different in composition than compartments containing solids. See, e.g., US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent which is not unit dosed may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and thus not a liquid, gel or powder at room temperature.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerin, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents such as EDTA and HEDP, perfumes and/or different type of fillers, surfactants, e.g., anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g., a two-stage vacuum plodder, extruders, cutters, logo-stampers, cooling tunnels and wrappers. A premix containing a soap, the enzyme of the invention, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

Enzymes in the form of granules, comprising an enzyme-containing core and optionally one or more coatings, are commonly used in granular (powder) detergents. Various methods for preparing the core are well-known in the art and include, for example, a) spray drying of a liquid enzyme-containing solution, b) production of layered products with an enzyme coated as a layer around a pre-formed inert core particle, e.g. using a fluid bed apparatus, c) absorbing an enzyme onto and/or into the surface of a pre-formed core, d) extrusion of an enzyme-containing paste, e) suspending an enzyme-containing powder in molten wax and atomization to result in prilled products, f) mixer granulation by adding an enzyme-containing liquid to a dry powder composition of granulation components, g) size reduction of enzyme-containing cores by milling or crushing of larger particles, pellets, etc., and h) fluid bed granulation. The enzyme-containing cores may be dried, e.g. using a fluid bed drier or other known methods for drying granules in the feed or enzyme industry, to result in a water content of typically 0.1-10% w/w water.

The enzyme-containing cores are optionally provided with a coating to improve storage stability and/or to reduce dust formation. One type of coating that is often used for enzyme granulates for detergents is a salt coating, typically an inorganic salt coating, which may e.g. be applied as a solution of the salt using a fluid bed. Other coating materials that may be used are, for example, polyethylene glycol (PEG), methyl hydroxy-propyl cellulose (MHPC) and polyvinyl alcohol (PVA). The granules may contain more than one coating, for example a salt coating followed by an additional coating of a material such as PEG, MHPC or PVA.

The present invention thus also relates to enzyme granules/particles comprising the subtilase of the invention. In an embodiment, the granule comprises a core, and optionally one or more coatings (outer layers) surrounding the core.

The core may have a diameter, measured as equivalent spherical diameter (volume based average particle size), of 20-2000 μm, particularly 50-1500 μm, 100-1500 μm or 250-1200 μm.

In an embodiment, the core comprises one or more polypeptides having protease activity of the present invention.

The core may include additional materials such as fillers, fiber materials (cellulose or synthetic fibers), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA).

The coating may be applied in an amount of at least 0.1% by weight of the core, e.g., at least 0.5%, at least 1%, at least 5%, at least 10%, or at least 15%. The amount may be at most 100%, 70%, 50%, 40% or 30%.

The coating is preferably at least 0.1 μm thick, particularly at least 0.5 μm, at least 1 μm or at least 5 μm. In some embodiments, the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should, in particular, be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

To provide acceptable protection, the salt coating is preferably at least 0.1 μm thick, e.g., at least 0.5 μm, at least 1 μm, at least 2 μm, at least 4 μm, at least 5 μm, or at least 8 µm. In a particular embodiment, the thickness of the salt coating is below 100 µm, such as below 60 µm, or below 40 µm.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular, having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20^\circ C.}$=76%), $Na_2CO_3$ ($CH_{20^\circ C.}$=92%), $NaNO_3$ ($CH_{20^\circ C.}$=73%), $Na_2HPO_4$ ($CH_{20^\circ C.}$=95%), $Na_3PO_4$ ($CH_{25^\circ C.}$=92%), $NH_4Cl$ ($CH_{20^\circ C.}$=79.5%), $(NH_4)_2HPO_4$ ($CH_{20^\circ C.}$=93.0%), $NH_4H_2PO_4$ ($CH_{20^\circ C.}$=93.1%), $(NH_4)_2SO_4$ ($CH_{20^\circ C.}$=81.1%), KCl ($CH_{20^\circ C.}$=85%), $K_2HPO_4$ ($CH_{20^\circ C.}$=92%), $KH_2PO_4$($CH_{20^\circ C.}$=96.5%), $KNO_3$ ($CH_{20^\circ C.}$=93.5%), $Na_2SO_4$ ($CH_{20^\circ C.}$=93%), $K_2SO_4$ ($CH_{20^\circ C.}$=98%), $KHSO_4$ ($CH_{20^\circ C.}$=86%), $MgSO_4$ ($CH_{20^\circ C.}$=90%), $ZnSO_4$ ($CH_{20^\circ C.}$=90%) and sodium citrate ($CH_{25^\circ C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granule may optionally have one or more additional coatings. Examples of suitable coating materials are polyethylene glycol (PEG), methyl hydroxy-propyl cellulose (MHPC) and polyvinyl alcohol (PVA). Examples of enzyme granules with multiple coatings are described in WO 93/07263 and WO 97/23606.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in the Handbook of Powder Technology; Particle size enlargement by C. E. Capes; Volume 1; 1980; Elsevier. Preparation methods include known feed and granule formulation technologies, e.g., (a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

(b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606.

(c) Absorbed core particles, wherein rather than coating the enzyme as a layer around the core, the enzyme is absorbed onto and/or into the surface of the core. Such a process is described in WO 97/39116.

(d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (Michael S. Showell (editor); *Powdered detergents*; Surfactant Science Series; 1998; vol. 71; pages 140-142; Marcel Dekker).

(e) Prilled products, wherein an enzyme-containing powder is suspended in molten wax and the suspension is sprayed, e.g., through a rotating disk atomizer, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. U.S. Pat. Nos. 4,016,040 and 4,713,245 describe this technique.

(f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process, various high-shear mixers can be used as granulators. Granulates consisting of enzyme, fillers and binders etc. are mixed with cellulose fibers to reinforce the particles to produce a so-called T-granulate. Reinforced particles are more robust, and release less enzymatic dust.

(g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in Martin Rhodes (editor); Principles of Powder Technology; 1990; Chapter 10; John Wiley & Sons.

(h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them to form a granule.

(i) The cores may be subjected to drying, such as in a fluid bed drier. Other known methods for drying granules in the feed or enzyme industry can be used by the skilled person. The drying preferably takes place at a product temperature of from 25 to 90° C. For some enzymes, it is important the cores comprising the enzyme contain a low amount of water before coating with the salt. If water sensitive enzymes are coated with a salt before excessive water is removed, it will be trapped within the core and may affect the activity of the enzyme negatively. After drying, the cores preferably contain 0.1-10% w/w water.

Non-dusting granulates may be produced, e.g., as disclosed in U.S. Pat. Nos. 4,106,991 and 4,661,452 and may optionally be coated by methods known in the art.

The granulate may further one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The enzyme may also be a protected enzyme prepared according to the method disclosed in EP 238,216.

In an embodiment, the granule further comprises one or more additional enzymes, e.g., hydrolase, isomerase, ligase, lyase, oxidoreductase, and transferase. The one or more additional enzymes are preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

For further information on enzyme granules and production thereof, see WO 2013/007594 as well as e.g. WO 2009/092699, EP 1705241, EP 1382668, WO 2007/001262, U.S. Pat. No. 6,472,364, WO 2004/074419 and WO 2009/102854.

Uses

The present invention is also directed to methods for using the subtilase variants according to the invention or compositions thereof in laundering of textile and fabrics, such as household laundry washing and industrial laundry washing.

The invention is also directed to methods for using the variants according to the invention or compositions thereof in cleaning hard surfaces such as floors, tables, walls, roofs etc. as well as surfaces of hard objects such as cars (car wash) and dishes (dishwashing).

The subtilase variants of the present invention may be added to and thus become a component of a detergent composition. Thus, one aspect of the invention relates to the use of a subtilase variant in a cleaning process such as laundering and/or hard surface cleaning.

A detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

The cleaning process or the textile care process may for example be a laundry process, a dishwashing process or cleaning of hard surfaces such as bathroom tiles, floors, table tops, drains, sinks and washbasins. Laundry processes can for example be household laundering, but may also be industrial laundering. Furthermore, the invention relates to a process for laundering of fabrics and/or garments, where the process comprises treating fabrics with a washing solution containing a detergent composition and at least one protease variant of the invention. The cleaning process or a textile care process can for example be carried out in a machine washing or manually. The washing solution can for example be an aqueous washing solution containing a detergent composition.

In one aspect, the subtilase variants of the invention are used in a cleaning process, e.g. a laundry process, that comprises a short wash cycle, typically a wash cycle of not more than about 30 minutes, such as not more than about 20 minutes, e.g. not more than about 15 minutes or not more than about 10 minutes. It has surprisingly been found that the subtilase variants of the invention are remarkably effective in short wash cycles lasting, for example, only about 10-20 minutes. This may e.g. be useful in top-loading washing machines that often have short wash cycles or for hand-washing of laundry.

In another aspect, the subtilase variants of the invention are used in a cleaning process, e.g. a laundry process, where the wash water is used for more than one portion of laundry. In this case, the wash water containing a detergent with a subtilase variant of the invention may be used in a first wash cycle for a first portion of laundry, and then reused one or more times for additional wash cycles with new portions of laundry. It has been found that detergents containing a subtilase variant of the invention are able to substantially maintain cleaning performance on protease-sensitive stains even after three wash cycles or more. This may for example be useful for laundry washed by hand and/or in regions with water scarcity.

The last few years there has been an increasing interest in replacing components in detergents that are derived from petrochemicals with renewable biological components such as enzymes and polypeptides without compromising the wash performance. When the components of detergent compositions change, new enzyme activities or new enzymes having alternative and/or improved properties compared to the previously used detergent enzymes such as proteases, lipases and amylases may be needed to achieve a similar or improved wash performance when compared to the traditional detergent compositions.

The invention further concerns the use of subtilase variants of the invention in a proteinaceous stain removing process. The proteinaceous stains may be stains such as food stains, e.g., baby food, cocoa, egg or milk, or other stains such as sebum, blood, ink or grass, or a combination hereof.

Washing Method

The present invention provides a method of cleaning a fabric, dishware or a hard surface with a detergent composition comprising a protease variant of the invention.

The method of cleaning comprises contacting an object with a detergent composition comprising a protease variant of the invention under conditions suitable for cleaning the object. In a preferred embodiment the detergent composition is used in a laundry or a dish wash process.

Another embodiment relates to a method for removing stains from fabric or dishware which comprises contacting the fabric or dishware with a composition comprising a protease of the invention under conditions suitable for cleaning the object. In the method of cleaning of the invention, the object being cleaned may be any suitable object such as a textile or a hard surface such as dishware or a floor, table, wall, etc.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The detergent compositions of the present invention are suited for use in laundry and hard surface applications, including dishwashing. Accordingly, the present invention includes a method for laundering a fabric or washing dishware, comprising contacting the fabric/dishware to be cleaned with a solution comprising the detergent composition according to the invention. The fabric may comprise any fabric capable of being laundered in normal consumer use conditions. The dishware may comprise any dishware such as crockery, cutlery, ceramics, plastics such as melamine, metals, china, glass and acrylics. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

The enzyme(s) of the detergent composition of the invention may be stabilized using conventional stabilizing agents and protease inhibitors, e.g., a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or CI2 or SSI. The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

The detergent compositions provided herein are typically formulated such that, during use in aqueous cleaning operations, the wash water has a pH of from about 5.0 to about 12.5, such as from about 5.0 to about 11.5, or from about 6.0 to about 10.5. In some embodiments, granular or liquid laundry products are formulated to have a pH from about 6 to about 8. Techniques for controlling pH at recommended usage levels include the use of buffers, alkalis, acids, etc., and are well known to those skilled in the art.

The present invention is further described by the following examples that should not be construed as limiting the scope of the invention.

EXAMPLES

Materials and Methods

Suc-AAPF-pNA Activity Assay

Proteolytic activity can be determined by a method employing Suc-AAPF-PNA as the substrate. Suc-AAPF-PNA is an abbreviation for N-Succinyl-Alanine-Alanine-Proline-Phenylalanine-p-Nitroanilide, and is a blocked peptide which can be cleaved by endo-proteases.

Following cleavage, a free PNA molecule is liberated which has a yellow color and thus can be measured by visible spectrophotometry at wavelength 405 nm. The Suc-AAPF-PNA substrate is manufactured by Bachem (cat. no. L1400, dissolved in DMSO).

The protease sample to be analyzed is diluted in residual activity buffer (100 mM Tris pH 8.6). The assay is performed by transferring 30 μl of diluted enzyme samples to 96 well microtiter plate and adding 70 μl substrate working solution (0.72 mg/ml in 100 mM Tris pH 8.6). The solution is mixed at room temperature and absorption is measured every 20 seconds over 5 minutes at OD 405 nm.

The slope (absorbance per minute) of the time-dependent absorption curve is directly proportional to the activity of the protease in question under the given set of conditions. The protease sample is diluted to a level where the slope is linear.

Example 1: Preparation and Purification of Polypeptides

Mutation and introduction of expression cassettes into *Bacillus subtilis* was performed by standard methods known in the art. All DNA manipulations were performed by PCR (e.g. as described by Sambrook et al., 2001, supra) using standard methods known to the skilled person.

Recombinant *B. subtilis* constructs encoding subtilase polypeptides were inoculated into and cultivated in a complex medium (TBgly) under antibiotic selection for 24h at 37° C. Shake flasks containing a rich media (PS-1: 100 g/L Sucrose (Danisco cat. no. 109-0429), 40 g/L crust soy (soy bean flour), 10 g/L $Na_2HPO_4.12H_2O$ (Merck cat. no. 106579), 0.1 ml/L Dowfax63N10 (Dow) were inoculated in a ratio of 1:100 with the overnight culture. Shake flask cultivation was performed for 4 days at 30° C. shaking at 270 rpm.

Purification of culture supernatants was performed as follows: The culture broth is centrifuged at 26000×g for 20 minutes and the supernatant is carefully decanted from the precipitate. The supernatant is filtered through a Nalgene 0.2 μm filtration unit in order to remove the remains of the host cells. The pH in the 0.2 μm filtrate is adjusted to pH 8 with 3 M Tris base and the pH-adjusted filtrate is applied to a MEP Hypercel column (Pall Corporation) equilibrated in 20 mM Tris/HCl, 1 mM $CaCl_2$, pH 8.0. After washing the column with the equilibration buffer, the column is step-eluted with 20 mM $CH_3COOH$/NaOH, 1 mM $CaCl_2$, pH 4.5. Fractions from the column are analyzed for protease activity using the Suc-AAPF-pNA assay at pH 9 and peak fractions are pooled. The pH of the pool from the MEP Hypercel column is adjusted to pH 6 with 20% (v/v) $CH_3COOH$ or 3 M Tris base and the pH-adjusted pool is diluted with deionized water to the same conductivity as 20 mM MES/NaOH, 2 mM $CaCl_2$, pH 6.0. The diluted pool is applied to an SP-Sepharose® Fast Flow column (GE Healthcare) equilibrated in 20 mM MES/NaOH, 2 mM $CaCl_2$, pH 6.0. After washing the column with the equilibration buffer, the protease variant is eluted with a linear NaCl gradient (0→0.5 M) in the same buffer over five column volumes. Fractions from the column are analyzed for protease activity using the Suc-AAPF-pNA assay at pH 9 and active fractions are analyzed by SDS-PAGE. Fractions in which only one band is observed on the Coomassie stained SDS-PAGE gel are pooled as the purified preparation and used for further experiments.

Example 2: Stability Assays at Different pH Values

The stability of variants of the invention was tested in an accelerated stability assay under two different sets of conditions: 1) in a low pH (4.0) stress buffer, and 2) in a high pH (10.5) stress buffer with LAS (linear alkylbenzene sulfonate).

Stability at Low pH

This assay at a low pH of 4.0 and in the absence of detergent is designed to simulate conditions during production of an enzyme granulate and in the granulate prior to addition to a detergent composition.

Purified protease samples are diluted with 0.01% Triton X-100 to 0.04 and 0.02 mg/ml. Then 180 μl low pH stress buffer (0.1M citric acid, 2 mM $CaCl_2$, 2 mM $MgSO_4$, pH 4.0) is mixed with 20 μl diluted protease in the well of a 96-well microtiter plate. After incubation at 37° C. in an Eppendorf Thermomixer with shaking for 0, 60 and 150 min, 20 μl is transferred to a new microtiter plate and mixed with 180 μl Suc-AAPF-pNA substrate solution (0.4 mg/ml Suc-AAPF-pNA in 0.1 M Tris pH 8.6). Activity is found by linear regression of the initial increase in absorbance at 405 nm measured every 20 seconds for 3 minutes in a plate reader (SpectraMax® Plus).

The half-life (T½) is calculated from linear regression of log(activity) versus incubation time. The measured half-life of a reference protease having SEQ ID NO: 1 with the substitutions S9R, P14H, R19L and N62D is set to 1, and half-life improvement factors (T½ IF) of other tested proteases are calculated as the half-life of a variant relative to the half-life of the reference protease.

Stability at High pH with LAS

This assay at a high pH of 10.5 and in the presence of LAS is designed to simulate conditions in a detergent composition, where the enzyme is in close contact with the detergent components.

Purified protease samples are diluted with 0.01% Triton X-100 to 0.04 and 0.02 mg/ml. Then 180 μl high pH stress buffer (0.1 M Na-carbonate, 2 mM $CaCl_2$, 2 mM $MgSO_4$, pH 10.5, 0.5% LAS (Thonyl P85 NaLAS)) is mixed with 20 μl diluted protease in the well of a 96-well microtiter plate. After incubation at 37° C. in an Eppendorf Thermomixer with shaking for 0, 60 and 150 min, 20 μl is transferred to a new microtiter plate and mixed with 180 μl Suc-AAPF-pNA substrate solution (0.4 mg/ml Suc-AAPF-pNA in 0.1 M Tris pH 8.6). Activity is found by linear regression of the initial increase in absorbance at 405 nm measured every 20 seconds for 3 minutes in a plate reader (SpectraMax® Plus).

The half-life (T½) is calculated from linear regression of log(activity) versus incubation time. The measured half-life of a reference protease having SEQ ID NO: 1 with the substitutions S9R, P14H, R19L and N62D is set to 1, and half-life improvement factors (T½ IF) of other tested proteases are calculated as the half-life of a variant relative to the half-life of the reference protease.

The half-life improvement factors of variants of the invention in both low pH and high pH+LAS stress buffer is given in Table 1 below, where it can be seen that the variants of the invention have excellent stability in both the low pH and the high pH+LAS conditions compared to the reference protease.

TABLE 1

Half-life improvement factor (T½ IF) of variants of the invention

| Variant | T½ IF Low pH | T½ IF High pH + LAS |
|---|---|---|
| Reference (SEQ ID NO: 1 + S9R P14H R19L N62D) | 1.0 | 1.0 |
| S3T S9R R19L N62D A194P | 8.8 | 3.2 |
| S3T S9R R19L N62D A194P Q245R S259D | 9.2 | 9.6 |
| S3T S9R R19L N43R N62D A194P R275Q | 12.5 | 3.5 |
| S3T S9R R19L N62D P131* A194P | 16.8 | 5.6 |
| S3T S9R R19L N62D P131* A194P Q245R S259D | 20.1 | 18.7 |
| S3T S9R R19L N43R N62D P131* A194P R275Q | 19.8 | 12.8 |
| S3T S9R R19L N43R N62D N76D A194P | 15.3 | 7.4 |
| S3T S9R R19L N43R N62D N76D P131* A194P | 24.8 | 7.6 |
| S3T S9R R19L N62D Q245R S259D | 7.5 | 5.8 |
| S3T S9R R19L N43R N62D R275Q | 8.7 | 2.5 |
| S3T S9R R19L N62D P131* | 13.5 | 4.2 |
| S3T S9R R19L N62D P131* Q245R S259D | 9.9 | 6.7 |
| S3T S9R R19L N43R N62D P131* R275Q | 16.0 | 5.7 |
| S3T S9R R19L N43R N62D N76D | 19.8 | 5.9 |

TABLE 1-continued

| Half-life improvement factor (T½ IF) of variants of the invention | | |
|---|---|---|
| Variant | T½ IF Low pH | T½ IF High pH + LAS |
| S3T S9R R19L N43R N62D N76D Q245R S259D | 23.5 | 15.9 |
| S3T S9R R19L N43R N62D N76D P131* | 16.9 | 9.0 |
| S9R A15T G61E N62D V68A A194P V205I Q245R N261D | 7.9 | 1.3 |
| S9R A15T G61E V68A A194P V205I Q245R S259D N261D | 6.2 | 1.6 |
| S9R R19L N43R N62D R275Q | 4.9 | 1.6 |
| S9R R19L N62D P131* | 7.3 | 1.9 |
| S3A S9R R19L N62D Q245R S259D | 2.9 | 2.1 |
| S3A S9R R19L N62D A194P | 3.5 | 1.2 |
| S9R R19L N43R N62D Q245R S259D R275Q | 5.9 | 5.3 |
| S9R R19L N62D P131* Q245R S259D | 9.2 | 7.5 |
| S9R R19L N43R N62D A194P R275Q | 6.8 | 2.6 |
| S9R R19L N62D P131* A194P | 10.7 | 5.2 |
| S9R R19L N43R N62D N76D | 12.8 | 5.0 |
| S3A S9R R19L N43R N62D Q245R S259D R275Q | 4.0 | 3.0 |
| S3A S9R R19L N62D P131* Q245R S259D | 6.2 | 6.8 |
| S3A S9R R19L N62D A194P Q245R S259D | 4.0 | 3.4 |
| S3A S9R R19L N43R N62D P131* R275Q | 6.6 | 2.2 |
| S3A S9R R19L N43R N62D A194P R275Q | 4.6 | 1.8 |
| S3A S9R R19L N62D P131* A194P | 7.4 | 3.0 |
| S3A S9R R19L N43R N62D N76D | 8.7 | 3.5 |
| S9R R19L N43R N62D P131* Q245R S259D R275Q | 12.9 | 8.8 |
| S9R R19L N43R N62D A194P Q245R S259D R275Q | 7.1 | 7.3 |
| S9R R19L N62D P131* A194P Q245R S259D | 11.3 | 11.4 |
| S9R R19L N43R N62D N76D Q245R S259D | 14.4 | 14.3 |
| S9R R19L N43R N62D P131* A194P R275Q | 14.4 | 6.2 |
| S9R R19L N43R N62D N76D P131* | 24.7 | 9.9 |
| S9R R19L N43R N62D N76D A194P | 16.9 | 8.7 |
| S3A S9R R19L N62D P131* A194P Q245R S259D | 9.1 | 4.8 |
| S3A S9R R19L N43R N62D N76D Q245R S259D | 10.9 | 9.4 |
| S3A S9R R19L N43R N62D P131* A194P R275Q | 9.8 | 4.5 |
| S3A S9R R19L N43R N62D N76D P131* | 17.8 | 8.2 |
| S3A S9R R19L N43R N62D N76D A194P | 12.6 | 8.4 |
| S9R R19L N43R N62D N76D P131* Q245R S259D | 16.8 | 17.7 |
| S9R R19L N43R N62D N76D A194P Q245R S259D | 12.6 | 18.7 |
| S9R R19L N43R N62D N76D P131* A194P | 16.6 | 9.8 |

Example 3: Automatic Mechanical Stress Assay (AMSA)

Wash performance of the selected proteases was initially tested using the Automatic Mechanical Stress Assay (AMSA). AMSA is a small-scale wash assay used to resemble full scale wash, which allows many proteases to be tested simultaneously due to the small well size and solution volume. In AMSA the detergent solution including protease is brought into contact with the textile by vigorously shaking of the test plate in a regular, oscillating manner to apply mechanical stress. For further description see WO 02/42740, especially the section “Special method embodiments” at page 23-24.

AMSA experiments were conducted using the experimental conditions listed in Table 2 below using the model laundry detergent for emerging markets (powder) as listed in Table 3. The standard textile swatches Chocolate milk with carbon black (PC-03) and Blood, milk, ink, extra heated (EMPA117EH) were obtained from Center For Testmaterials B.V. (CFT, Stoomloggerweg 11, 3133 KT Vlaardingen, The Netherlands) and Swissatest Testmaterialien AG (Mövenstrasse 12, 9015 St. Gallen, Switzerland), respectively.

TABLE 2

| AMSA experimental conditions | |
|---|---|
| Detergent | Model laundry detergent for emerging market (powder) |
| Detergent dosage | 2.0 g/L |
| Water hardness | 9° dH |
| Water hardness ratio | 2:1:4.5 ($Ca^{2+}$:$Mg^{2+}$:$CO_3^{2}$) |
| pH | 10.2 |
| Protease concentration | 0.26 and 0.52 mg enzyme protein/L (10 and 20 nM) |
| Test solution volume | 160 μL |
| Wash time | 20 minutes |
| Wash temperature | 25° C. |
| Textile swatches | Chocolate milk with carbon black (PC-03, CFT) Blood, milk, ink, extra heated (EMPA117EH, Swissatest) |

TABLE 3

| Ingredient list for model laundry detergent for emerging market (powder) | |
|---|---|
| Ingredient | Content (w/w %)* |
| LAS, sodium salt | 15.0% |
| Nonionic surfactant (alcohol ethoxylate; AEO) | 2.0% |
| Soda ash | 20.1% |
| Hydrous sodium silicate | 9.9% |
| Zeolite 4A+ | 12.1% |
| PCA (copoly(acrylic acid/maleic acid), sodium salt | 1.3% |
| Sodium sulfate | 31.4% |

*The amounts in Table 3 correspond to the amount of active component in the ingredients. The remainder, approx. 8%, consists of the inactive part of the ingredients, primarily water.

Following the AMSA wash, textile swatches were rinsed in water, dried, and scanned using a flatbed scanner (Epson Expression 10000XL). The cleanness of the textile swatches and thus the individual protease wash performance was determined by calculating the intensity of the reflected light from the scanned images. A special designed software application is used (Novozymes Color Vector Analyzer). The program retrieves 24-bit pixel values from the image and converts them into values for red, green and blue (RGB). The intensity value is calculated by adding the RGB values together as vectors and then taking the length of the resulting vector using this formula:

$$\text{Intensity}=\sqrt{r^2+g^2+b^2}.$$

Table 4 below provides information on the wash performance of variants of the invention in AMSA on the two stains EMPA117EH and PC-03 in two different protease concentrations, expressed as relative wash performance compared to that of the reference protease having SEQ ID NO: 1. The relative wash performance values in Table 4 were calculated by 1) obtaining an intensity value improvement over blank by deducting the calculated intensity value of a blank, i.e. a stain washed with the model detergent without an enzyme, from the calculated intensity value for a variant or the reference protease, and then 2) dividing the wash performance of the variants (intensity value improvement over blank) by the wash performance of the reference (intensity value improvement over blank), in other words:

$$(\text{Intensity}_{variant}-\text{Intensity}_{blank})/(\text{Intensity}_{reference}-\text{Intensity}_{blank})$$

The AMSA wash results in Table 4 below show that the variants of the invention have a substantially improved wash performance on EMPA117EH compared to the reference protease. Similarly, for PC-03 the wash performance of the variants of the invention is in most cases better than that of the reference protease.

TABLE 4

Relative wash performance in AMSA; improvement over blank relative to SEQ ID NO: 1

| Variant | EMPA117EH 10 nM | EMPA117EH 20 nM | PC-03 10 nM | PC-03 20 nM |
|---|---|---|---|---|
| Reference (Savinase ®; SEQ ID NO: 1) | 1.00 | 1.00 | 1.00 | 1.00 |
| S3T S9R R19L N62D A194P | 1.49 | 1.40 | 1.33 | 1.23 |
| S3T S9R R19L N62D A194P Q245R S259D | 1.54 | 1.52 | 1.58 | 1.50 |
| S3T S9R R19L N43R N62D A194P R275Q | 1.46 | 1.38 | 1.46 | 1.33 |
| S3T S9R R19L N62D P131* A194P | 1.51 | 1.38 | 1.04 | 1.07 |
| S3T S9R R19L N62D P131* A194P Q245R S259D | 1.49 | 1.40 | 1.00 | 1.13 |
| S3T S9R R19L N43R N62D P131* A194P R275Q | 1.49 | 1.33 | 0.96 | 1.00 |
| S3T S9R R19L N43R N62D N76D A194P | 1.51 | 1.38 | 1.42 | 1.30 |
| S3T S9R R19L N43R N62D N76D P131* A194P | 1.54 | 1.48 | 1.04 | 1.13 |
| S3T S9R R19L N62D Q245R S259D | 1.60 | 1.52 | 1.46 | 1.30 |
| S3T S9R R19L N43R N62D R275Q | 1.43 | 1.36 | 1.33 | 1.27 |
| S3T S9R R19L N62D P131* | 1.57 | 1.52 | 1.17 | 1.20 |
| S3T S9R R19L N62D P131* Q245R S259D | 1.74 | 1.64 | 1.75 | 1.63 |
| S3T S9R R19L N43R N62D P131* R275Q | 1.51 | 1.45 | 1.21 | 1.17 |
| S3T S9R R19L N43R N62D N76D | 1.49 | 1.43 | 1.46 | 1.37 |
| S3T S9R R19L N43R N62D N76D Q245R S259D | 1.60 | 1.50 | 1.46 | 1.40 |
| S3T S9R R19L N43R N62D N76D P131* | 1.51 | 1.43 | 1.04 | 1.17 |
| S9R A15T G61E N62D V68A A194P V205I Q245R N261D | 1.83 | 1.69 | 1.58 | 1.40 |
| S9R A15T G61E V68A A194P V205I Q245R S259D N261D | 1.63 | 1.50 | 1.33 | 1.23 |
| S9R R19L N43R N62D R275Q | 1.49 | 1.40 | 1.46 | 1.33 |
| S9R R19L N62D P131* | 1.60 | 1.50 | 1.17 | 1.13 |
| S3A S9R R19L N62D Q245R S259D | 1.60 | 1.52 | 1.50 | 1.43 |
| S3A S9R R19L N62D A194P | 1.46 | 1.36 | 1.33 | 1.30 |
| S9R R19L N43R N62D Q245R S259D R275Q | 1.54 | 1.45 | 1.42 | 1.27 |
| S9R R19L N62D P131* Q245R S259D | 1.66 | 1.57 | 1.08 | 1.20 |
| S9R R19L N43R N62D A194P R275Q | 1.43 | 1.36 | 1.29 | 1.23 |
| S9R R19L N62D P131* A194P | 1.49 | 1.45 | 1.17 | 1.23 |
| S9R R19L N43R N62D N76D | 1.49 | 1.40 | 1.46 | 1.37 |
| S3A S9R R19L N43R N62D Q245R S259D R275Q | 1.49 | 1.40 | 1.46 | 1.37 |
| S3A S9R R19L N62D P131* Q245R S259D | 1.51 | 1.43 | 1.08 | 1.13 |
| S3A S9R R19L N62D A194P Q245R S259D | 1.51 | 1.43 | 1.42 | 1.30 |
| S3A S9R R19L N43R N62D P131* R275Q | 1.40 | 1.36 | 1.00 | 1.07 |
| S3A S9R R19L N43R N62D A194P R275Q | 1.43 | 1.33 | 1.38 | 1.33 |
| S3A S9R R19L N62D P131* A194P | 1.54 | 1.45 | 1.17 | 1.20 |
| S3A S9R R19L N43R N62D N76D | 1.49 | 1.38 | 1.46 | 1.33 |
| S9R R19L N43R N62D P131* Q245R S259D R275Q | 1.43 | 1.38 | 0.96 | 1.03 |
| S9R R19L N43R N62D A194P Q245R S259D R275Q | 1.57 | 1.45 | 1.46 | 1.37 |
| S9R R19L N62D P131* A194P Q245R S259D | 1.49 | 1.43 | 1.13 | 1.17 |
| S9R R19L N43R N62D N76D Q245R S259D | 1.63 | 1.48 | 1.42 | 1.33 |
| S9R R19L N43R N62D P131* A194P R275Q | 1.49 | 1.40 | 1.08 | 1.13 |
| S9R R19L N43R N62D N76D P131* | 1.51 | 1.52 | 1.00 | 1.13 |
| S9R R19L N43R N62D N76D A194P | 1.49 | 1.40 | 1.42 | 1.33 |
| S3A S9R R19L N62D P131* A194P Q245R S259D | 1.51 | 1.48 | 1.13 | 1.20 |
| S3A S9R R19L N43R N62D N76D Q245R S259D | 1.63 | 1.55 | 1.50 | 1.43 |
| S3A S9R R19L N43R N62D P131* A194P R275Q | 1.49 | 1.40 | 1.08 | 1.10 |
| S3A S9R R19L N43R N62D N76D P131* | 1.46 | 1.43 | 0.92 | 1.03 |
| S3A S9R R19L N43R N62D N76D A194P | 1.49 | 1.40 | 1.46 | 1.33 |
| S9R R19L N43R N62D N76D P131* Q245R S259D | 1.57 | 1.48 | 1.08 | 1.13 |
| S9R R19L N43R N62D N76D A194P Q245R S259D | 1.54 | 1.40 | 1.38 | 1.30 |
| S9R R19L N43R N62D N76D P131* A194P | 1.51 | 1.43 | 1.04 | 1.10 |

Example 4: Terg-O-toMeter (TOM) Wash

Wash performance of the selected proteases was further tested in the medium-scale Terg-O-toMeter (TOM) wash assay, in which more textile swatch types can be tested. A TOM is basically a large temperature-controlled water bath with up to 16 open metal beakers submerged into it. Each beaker constitutes a small top-loader style washing machine, and during an experiment each of them will contain a solution of a specific detergent/enzyme system together with soiled and unsoiled fabrics whose performance is tested. A rotating stirring arm within each beaker is used to create mechanical stress, generally at 120 rpm. The TOM provides a link between small-scale experiments, such as AMSA, and more time-consuming and costly full-scale wash experiments in full-size washing machines.

TOM experiments were conducted using the experimental conditions listed in Table 5 using the model laundry detergent for emerging markets (powder) as listed in Table 3 above. The standard textile swatches were obtained either from Center For Testmaterials B.V. (CFT, Stoomloggerweg 11, 3133 KT Vlaardingen. The Netherlands) or from Swissatest Testmaterialien AG (Mövenstrasse 12, 9015 St. Gallen, Switzerland).

TABLE 5

| TOM experimental conditions | |
|---|---|
| Detergent | Model laundry detergent for emerging market (powder) |
| Detergent dosage | 2.0 g/L |
| Water hardness | 9° dH |
| Water hardness ratio | 2:1:4.5 ($Ca^{2+}$:$Mg^{2+}$:$CO_3^{2}$) |
| pH | 10.2 |
| Protease concentration | 0.13 mg enzyme protein/L (5 nM) |
| Test solution volume | 1 L |
| Stirring rate | 120 rpm |
| Wash time | 20 minutes |
| Wash temperature | 25° C. |
| Textile swatches | Chocolate milk with carbon black (PC-03, CFT)<br>Blood, milk, ink (PC-05, CFT)<br>Blood, milk, ink, (EMPA116, Swissatest)<br>Blood, milk, ink, extra heated (EMPA117EH, Swissatest) |

Following the TOM wash, textile swatches were rinsed in water and dried. Cleanness of the textile swatches and thus individual protease wash performance was determined by measuring the light remission at 460 nm using a Macbeth Color-Eye 7000 Spectrophotometer.

The measured remission values are used to calculate a Delta remission value (ΔRem), which is defined herein as the result of a reflectance or remission measurement of a sample swatch at a certain wavelength, in this case 460 nm, minus the remission value of a reference swatch, which in the present example is a swatch washed with the same detergent without an enzyme (blank). The results of the TOM assay are shown in Table 6 below. Table 7 shows the same results, but with the wash performance values for SEQ ID NO: 1 set to 1, and with the relative wash performance values of the variants calculated compared to SEQ ID NO: 1.

TABLE 6

Wash performance in TOM assay. Delta remission compared to blank

| | Stain: | | | |
|---|---|---|---|---|
| Variant: | PC-03 | PC-05 | EMPA116 | EMPA117EH |
| Blank (no enzyme) | 0 | 0 | 0 | 0 |
| Reference 1 (SEQ ID NO: 1) | 2.54 | 4.81 | 6.71 | 6.00 |
| Reference 2 (SEQ ID NO: 1 + S9R + P14H + R19L + N62D) | 6.64 | 8.96 | 9.67 | 15.15 |
| S3T + S9R + R19L + N62D + A194P | 5.85 | 9.91 | 9.96 | 14.85 |
| S3T + S9R + R19L + N62D + A194P + Q245R + S259D | 6.98 | 8.67 | 8.88 | 15.32 |
| S3T + S9R + R19L + N62D + A194P + R275RHHHH | 6.77 | 9.87 | 9.07 | 15.27 |

TABLE 7

Relative wash performance in TOM assay of variants compared to reference (SEQ ID NO: 1) based on Table 6

| | Stain: | | | |
|---|---|---|---|---|
| Variant: | PC-03 | PC-05 | EMPA116 | EMPA117EH |
| Blank (no enzyme) | 0 | 0 | 0 | 0 |
| Reference 1 (SEQ ID NO: 1) | 1.00 | 1.00 | 1.00 | 1.00 |
| Reference 2 (SEQ ID NO: 1 + S9R + P14H + R19L + N62D) | 2.61 | 1.86 | 1.44 | 2.53 |
| S3T + S9R + R19L + N62D + A194P | 2.30 | 2.06 | 1.48 | 2.48 |
| S3T + S9R + R19L + N62D + A194P + Q245R + S259D | 2.75 | 1.80 | 1.32 | 2.55 |
| S3T + S9R + R19L + N62D + A194P + R275RHHHH | 2.67 | 2.05 | 1.35 | 2.55 |

The TOM assay data in Tables 6 and 7 shows that the protease variants of the invention have a wash performance that is substantially improved over that of the protease of SEQ ID NO: 1 and on par with that of the high-performing but unstable variant of SEQ ID NO: 1 with the substitutions S9R+P14H+R19L+N62D.

Example 5: Wash Performance in Short Wash Cycles, Latin American Conditions

The wash performance of a variant of the invention on a stain set composed of 8 different protease-sensitive stains was tested in the TOM assay described in Example 4, under Latin American conditions using a Latin American powder laundry detergent base from Brazil without enzymes.

The test was performed with a wash temperature of 25° C., no soaking, and a main wash cycle of 12, 15 or 20 min. with agitation at 100 cycles/min. The water hardness was 5.6° dH ($Ca^{2+}$/$Mg^{2+}$/$HCO_3^-$ ratio 2:1:4.5), with a detergent dose of 2.5 g/L. The protease dose was 10 nM.

The stain set was composed of 8 protease-sensitive stains, available from Center For Testmaterials B.V. (CFT, Stoomloggerweg 11, 3133 KT Vlaardingen. The Netherlands) or from Swissatest Testmaterialien AG (Mövenstrasse 12, 9015 St. Gallen, Switzerland).

After wash, protease wash performance on the test swatches was determined by measuring the light remission at 460 nm as described in Example 4, and calculating a Delta remission value as the remission measurement of a sample swatch minus the remission value of a reference swatch washed with the same detergent but without an enzyme (blank).

Table 8 below shows the sum of the 8 Delta values compared to blank for the reference protease (SEQ ID NO: 1) and a protease of the invention (SEQ ID NO: 1+S3T+S9R+R19L+N62D+A194P) determined in short wash cycles of 12, 15 and 20 minutes, respectively.

TABLE 8

Sum of delta values compared to blank for 8 protease-sensitive stains

| | 12 min. | 15 min. | 20 min. |
|---|---|---|---|
| Reference (SEQ ID NO: 1) | 65 | 81 | 87 |
| S3T + S9R + R19L + N62D + A194P | 83 | 98 | 97 |

Example 6: Wash Performance in Dirty Wash Water, Chinese Conditions

The wash performance of a variant of the invention on a stain set composed of 7 different protease-sensitive stains was tested in the TOM assay described in Example 4, under Chinese conditions using a commercially available Chinese powder laundry detergent from Liby.

The test was performed with a wash temperature of 25° C., without soaking, performing three rounds of washes with a wash time of 20 min. each in the same wash solution. After each of the first and second wash cycles, the washed stain swatches were removed and discarded, and new stain swatches were added for a further wash cycle in the same (dirty) wash water. After the third wash cycle, the swatches were rinsed and dried as described in Example 4, and the remission was measured.

The water hardness was 14° dH ($Ca^{2+}/Mg^{2+}/HCO_3^-$ ratio 3:2:0), with a detergent dose of 2 g/L. The test was performed with two different proteases doses, 9 nM and 12 nM. The stain set was composed of 7 protease-sensitive stains, available from Center For Testmaterials B.V. (CFT, Stoomloggerweg 11, 3133 KT Vlaardingen. The Netherlands) or from Swissatest Testmaterialien AG (Mövenstrasse 12, 9015 St. Gallen, Switzerland).

After the third wash cycle, protease wash performance on the third set of test swatches was determined by measuring the light remission at 460 nm as described in Example 4, and calculating a Delta remission value as the remission measurement of a sample swatch minus the remission value of a reference swatch washed with the same detergent but without an enzyme (blank).

Table 9 below shows the sum of the 7 Delta values compared to blank for the reference protease (SEQ ID NO: 1) and a protease of the invention (SEQ ID NO: 1+S3T+S9R+R19L+N62D+A194P) determined in the third set of test swatches washed in dirty water in which two wash cycles had already been performed.

TABLE 9

| | Sum of delta values compared to blank for 7 protease-sensitive stains | |
|---|---|---|
| | 9 nM protease | 12 nM protease |
| Reference (SEQ ID NO: 1) | 18 | 21 |
| S3T + S9R + R19L + N62D + A194P | 36 | 43 |

Example 7: Wash Performance in Dirty Wash Water, Southeast Asian Conditions

The wash performance of a variant of the invention on a stain set composed of 8 different protease-sensitive stains was tested in the TOM assay described in Example 4 under Southeast Asian conditions using a powder laundry detergent base from Indonesia without enzymes.

The test was performed with a wash temperature of 25° C., without soaking, performing three rounds of washes each consisting of a 20 min. main wash in the same wash solution using 30 g of ballast. After each of the first and second wash cycles, the washed stain swatches were removed and discarded, and new stain swatches were added for a further cycle of soaking and washing in the same (dirty) wash water. After the third wash cycle, the swatches were rinsed and dried as described in Example 4, and the remission was measured.

The water hardness was 5.6° dH ($Ca^{2+}/Mg^{2+}/HCO_3^-$ ratio 2:1:4.5), with a detergent dose of 2 g/L. The test was performed with three different proteases doses, 3.4 nM, 4.4 nM and 5.7 nM. The stain set was composed of 8 protease-sensitive stains, available from Center For Testmaterials B.V. (CFT, Stoomloggerweg 11, 3133 KT Vlaardingen. The Netherlands) or from Swissatest Testmaterialien AG (Mövenstrasse 12, 9015 St. Gallen, Switzerland).

After the third wash cycle, protease wash performance on the third set of test swatches was determined by measuring the light remission at 460 nm as described in Example 4, and calculating a Delta remission value as the remission measurement of a sample swatch minus the remission value of a reference swatch washed with the same detergent but without an enzyme (blank).

Table 10 below shows the sum of the 8 Delta values compared to blank for the reference protease (SEQ ID NO: 1) and a protease of the invention (SEQ ID NO: 1+S3T+S9R+R19L+N62D+A194P) determined in the third set of test swatches washed in dirty water in which two wash cycles had already been performed.

TABLE 10

| | Sum of delta values compared to blank for 8 protease-sensitive stains | | |
|---|---|---|---|
| | 3.4 nM protease | 4.4 nM protease | 5.7 nM protease |
| Reference (SEQ ID NO: 1) | 45 | 54 | 57 |
| S3T + S9R + R19L + N62D + A194P | 70 | 78 | 79 |

The invention claimed is:

1. A subtilase variant comprising the substitutions X9R+X19L+X62D, wherein (a) position numbers correspond to positions of the polypeptide of SEQ ID NO: 2;

(b) the variant has protease activity; and (c) the variant has at least 80% but less than 100% sequence identity to the polypeptide of SEQ ID NO: 1;

and with the proviso that the variant does not comprise a histidine residue in position 14.

2. The subtilase variant of claim 1, comprising the substitutions S9R+R19L+N62D, and further comprising at least one alteration selected from the group consisting of S3T, S3A, N43R, V68A, N76D, P131*, A194P, V205I, Q245R, S259D, N261D and R275Q, wherein position numbers correspond to positions of the polypeptide of SEQ ID NO: 2.

3. The subtilase variant of claim 2, wherein the variant comprises a set of alterations selected from the group consisting of:

S3T+S9R+R19L+N62D+A194P;
S3T+S9R+R19L+N62D+A194P+Q245R+S259D;
S3T+S9R+R19L+N43R+N62D+A194P+R275Q;
S3T+S9R+R19L+N62D+P131*+A194P;
S3T+S9R+R19L+N62D+P131*+A194P+Q245R+S259D;
S3T+S9R+R19L+N43R+N62D+P131*+A194P+R275Q;
S3T+S9R+R19L+N43R+N62D+N76D+A194P;
S3T+S9R+R19L+N43R+N62D+N76D+P131*+A194P,
S3T+S9R+R19L+N62D+Q245R+S259D;
S3T+S9R+R19L+N43R+N62D+R275Q;
S3T+S9R+R19L+N62D+P131 *;
S3T+S9R+R19L+N62D+P131*+Q245R+S259D;
S3T+S9R+R19L+N43R+N62D+P131*+R275Q;
S3T+S9R+R19L+N43R+N62D+N76D;
S3T+S9R+R19L+N43R+N62D+N76D+Q245R+S259D;
S3T+S9R+R19L+N43R+N62D+N76D+P131 *;
S9R+A15T+G61E+N62D+V68A+A194P+V205I+Q245R+N261D;
S9R+A15T+G61E+V68A+A194P+V205I+Q245R+S259D+N261D;
S9R+R19L+N43R+N62D+R275Q;
S9R+R19L+N62D+P131 *;
S3A+S9R+R19L+N62D+Q245R+S259D;
S3A+S9R+R19L+N62D+A194P;
S9R+R19L+N43R+N62D+Q245R+S259D+R275Q;
S9R+R19L+N62D+P131*+Q245R+S259D;
S9R+R19L+N43R+N62D+A194P+R275Q;
S9R+R19L+N62D+P131*+A194P;
S9R+R19L+N43R+N62D+N76D;
S3A+S9R+R19L+N43R+N62D+Q245R+S259D+R275Q;
S3A+S9R+R19L+N62D+P131*+Q245R+S259D;
S3A+S9R+R19L+N62D+A194P+Q245R+S259D;
S3A+S9R+R19L+N43R+N62D+P131*+R275Q;
S3A+S9R+R19L+N43R+N62D+A194P+R275Q;
S3A+S9R+R19L+N62D+P131*+A194P;
S3A+S9R+R19L+N43R+N62D+N76D;
S9R+R19L+N43R+N62D+P131*+Q245R+S259D+R275Q;
S9R+R19L+N43R+N62D+A194P+Q245R+S259D+R275Q; and
S9R+R19L+N62D+P131*+A194P+Q245R+S259D.

4. The subtilase variant of claim 3, wherein the variant comprises SEQ ID NO: 1 with one of said sets of alterations.

5. The subtilase variant of claim 1, wherein the variant comprises the substitutions X3T+X9R+X19L+X62D+X194P.

6. The subtilase variant of claim 5, wherein the variant comprises SEQ ID NO: 1 with the substitutions S3T+S9R+R19L+N62D+A194P.

7. The subtilase variant of claim 5, further comprising at least one alteration selected from the group consisting of N43R, N76D, P131*, Q245R, S259D and R275Q, wherein position numbers correspond to positions of the polypeptide of SEQ ID NO: 2.

8. The subtilase variant of claim 7, comprising the substitutions Q245R+S259D.

9. The subtilase variant of claim 8, wherein the variant comprises SEQ ID NO: 1 with the substitutions S3T+S9R+R19L+N62D+A194P+Q245R+S259D.

10. The subtilase variant of claim 1, comprising the substitutions S3T+S9R+R19L+N62D+A194P.

11. The subtilase variant of claim 1, wherein the variant has at least 85%, but less than 100% sequence identity to the polypeptide of SEQ ID NO: 1.

12. The subtilase variant of claim 11, wherein the variant has at least 90%, at least 91%, at least 92%, at least 93%, at least 94%, at least 95%, at least 96% or at least 97% but less than 100% sequence identity to the polypeptide of SEQ ID NO: 1.

13. The subtilase variant of claim 1, wherein the variant has an improved stability in varied pH conditions compared to a reference protease having SEQ ID NO: 1 with the substitutions S9R+P14H+R19L+N62D.

14. The subtilase variant of claim 1, wherein the variant has an improved wash performance on a textile stain compared to the polypeptide of SEQ ID NO: 1.

15. The subtilase variant of claim 14, wherein the textile stain comprises blood, milk and ink.

16. A granule comprising:

(a) a core comprising the subtilase variant of claim 1, and optionally (b) a coating consisting of one or more layer(s) surrounding the core.

17. A detergent composition comprising a subtilase variant of claim 1, and at least one detergent component.

18. A method of cleaning laundry or a hard surface, the method comprising contacting an object with a subtilase variant of claim 1 under conditions suitable for cleaning the object.

19. The method of claim 18, wherein the cleaning is dishwashing.

20. A method for obtaining a subtilase variant, the method comprising:

(a) providing a host cell comprising a polynucleotide encoding a variant of a parent protease comprising the mutations X9R+X19L+X62D compared to SEQ ID NO: 1, wherein position numbers correspond to positions of the polypeptide of SEQ ID NO: 2, wherein the variant has protease activity and a sequence identity to SEQ ID NO: 1 of at least 80% but less than 100%, and with the proviso that the variant does not comprise a histidine residue in position 14;

(b) cultivating the host cell under conditions suitable for expression of the variant; and (c) recovering the variant.

* * * * *

SEQUENCE LISTING

```
<160> NUMBER OF SEQ ID NOS: 2

<210> SEQ ID NO 1
<211> LENGTH: 269
<212> TYPE: PRT
<213> ORGANISM: Bacillus lentus

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

-continued

```
Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 2
<211> LENGTH: 275
<212> TYPE: PRT
<213> ORGANISM: Bacillus amyloliquefaciens

<400> SEQUENCE: 2

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140
```

-continued

```
Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```